US009846171B2

(12) United States Patent
Yoshikawa et al.

(10) Patent No.: US 9,846,171 B2
(45) Date of Patent: Dec. 19, 2017

(54) AUTOMATED ANALYZER

(71) Applicant: HITACHI HIGH-TECHNOLOGIES COPRORATION, Tokyo (JP)

(72) Inventors: Keiko Yoshikawa, Tokyo (JP); Akihisa Makino, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/651,026

(22) PCT Filed: Dec. 13, 2013

(86) PCT No.: PCT/JP2013/083406
§ 371 (c)(1),
(2) Date: Jun. 10, 2015

(87) PCT Pub. No.: WO2014/097973
PCT Pub. Date: Jun. 26, 2014

(65) Prior Publication Data
US 2015/0316570 A1 Nov. 5, 2015

(30) Foreign Application Priority Data
Dec. 19, 2012 (JP) ................................ 2012-276355

(51) Int. Cl.
G01N 35/10 (2006.01)
G01N 35/00 (2006.01)
B01F 3/08 (2006.01)

(52) U.S. Cl.
CPC ... *G01N 35/1002* (2013.01); *G01N 35/00722* (2013.01); *G01N 35/1016* (2013.01);
(Continued)

(58) Field of Classification Search
CPC ..... G01N 35/1016; G01N 2035/00544; G01N 2035/1058; B01F 3/0865
See application file for complete search history.

(56) References Cited

U.S. PATENT DOCUMENTS

2002/0014496 A1* 2/2002 Cline .................... B01F 5/0615
222/1
2006/0039824 A1* 2/2006 Onuma ................... B01L 3/021
422/67
2008/0236301 A1* 10/2008 Fukushima ........ G01N 35/1016
73/863

FOREIGN PATENT DOCUMENTS

EP 1 890 158 A1 2/2008
JP 56-164957 * 12/1981
(Continued)

OTHER PUBLICATIONS

International Search Report.
(Continued)

*Primary Examiner* — P. Kathryn Wright
(74) *Attorney, Agent, or Firm* — Mattingly & Malur, PC

(57) ABSTRACT

A control section causes one dispensing mechanism of either a reagent dispensing mechanism or a sample dispensing mechanism to first discharge a predetermined amount of a liquid into the reaction container, and then, with respect to the cases where the amount of a liquid to be discharged by the other dispensing mechanism is larger or smaller than the amount of the liquid in the reaction container, causes the other dispensing mechanism to discharge the liquid such that the discharge speed in the case where the amount of the liquid to be discharged is larger is decreased relative to the discharge speed in the case where the amount of the liquid to be discharged is smaller.

19 Claims, 5 Drawing Sheets

(52) U.S. Cl.
CPC .... *B01F 3/0865* (2013.01); *G01N 2035/0091* (2013.01); *G01N 2035/00544* (2013.01); *G01N 2035/00891* (2013.01); *G01N 2035/1018* (2013.01); *G01N 2035/1058* (2013.01)

(56) References Cited

FOREIGN PATENT DOCUMENTS

| | | |
|---|---|---|
| JP | 10-73532 A | 3/1998 |
| JP | 10-73540 A | 3/1998 |
| JP | 2001-83165 A | 3/2001 |
| JP | 2006-343242 A | 12/2006 |
| JP | 2011-128075 A | 6/2011 |
| WO | 2014/097973 A1 | 6/2014 |

OTHER PUBLICATIONS

Extended European Search Report received in corresponding European Application No. 13865612.9 dated Jul. 14, 2016.
Japanese Office Action received in corresponding Japanese Application No. 2016-065011 dated Feb. 28, 2017.

\* cited by examiner

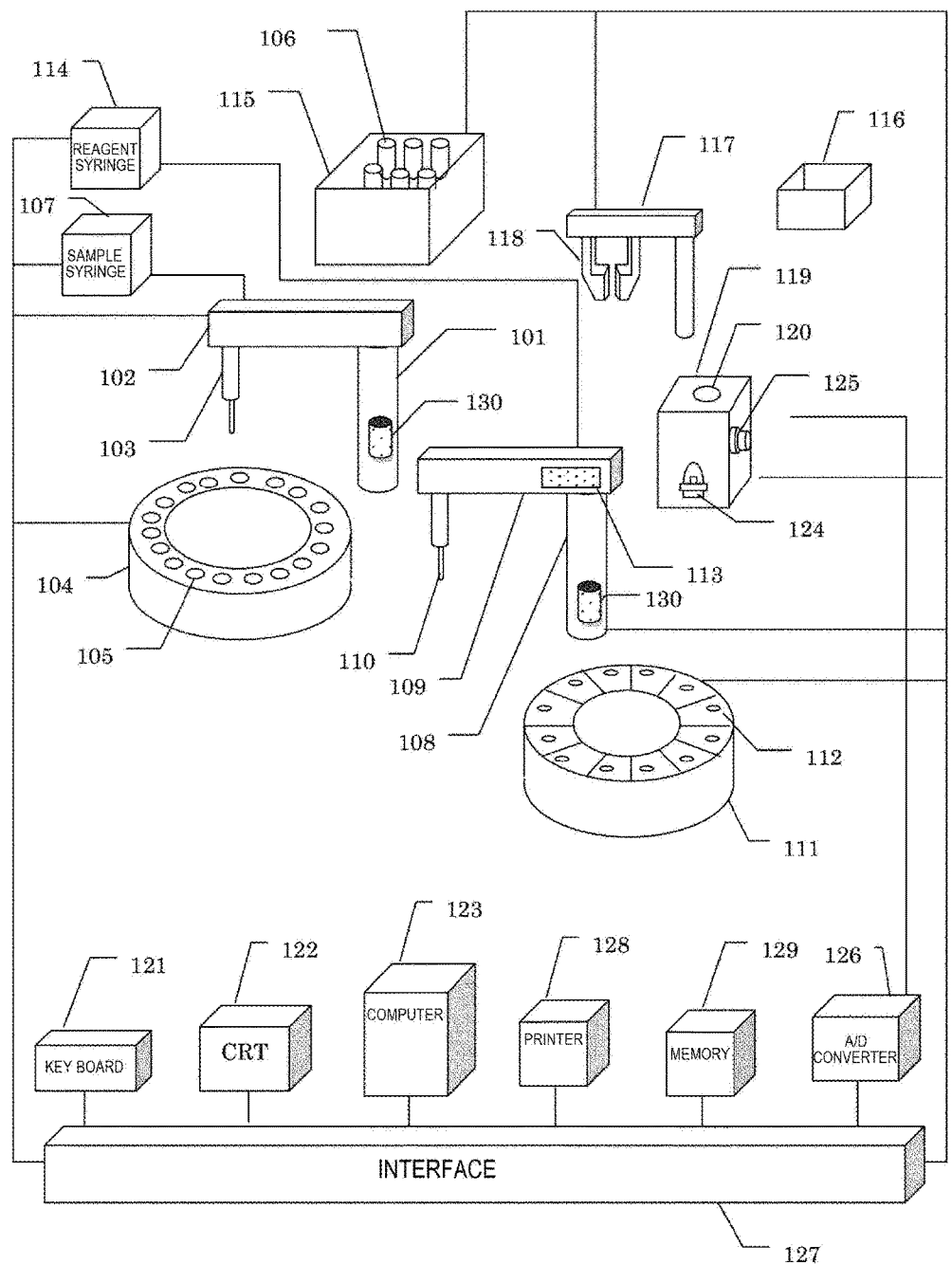
[FIG. 1]

[FIG. 2]
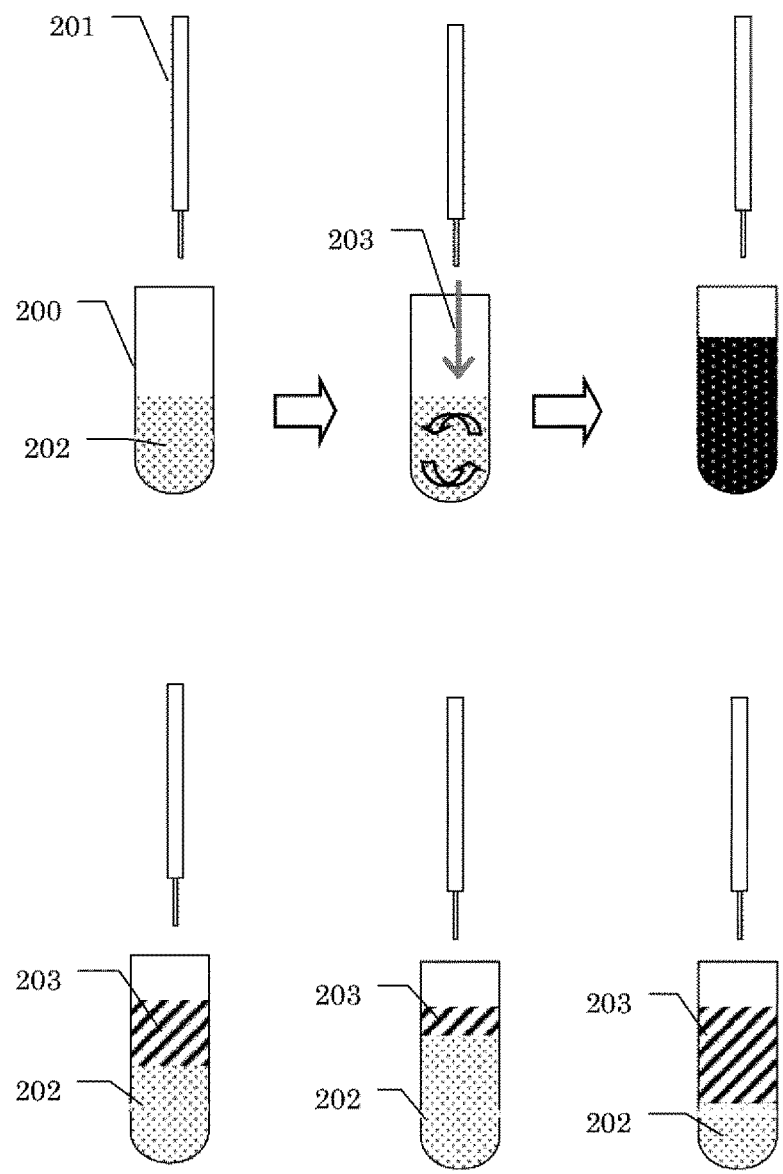

[FIG. 3]
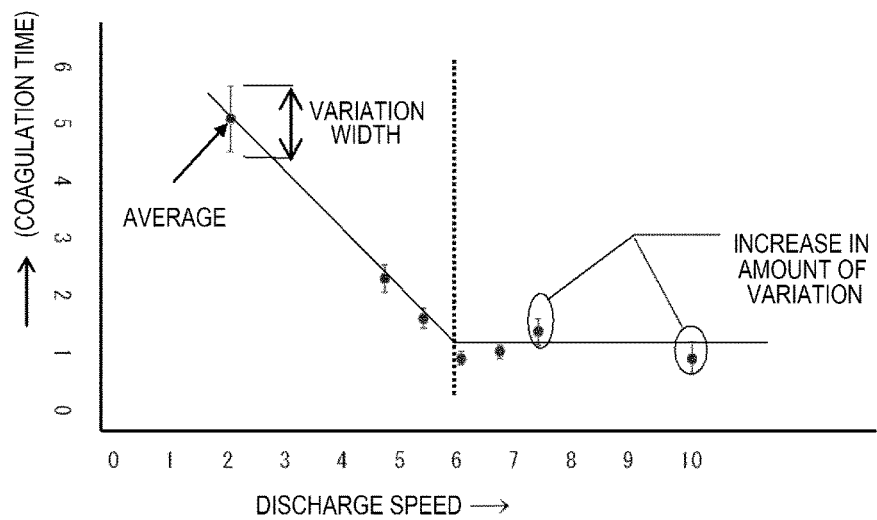
[FIG. 4]
| Amount of first dispensed liquid | Amount of secondarily dispensed liquid | Discharge speed |
|---|---|---|
| 1 | 10 | Extremely low |
| 1 | 5 | Very low |
| 1 | 2 | Low |
| 1 | 1 | Medium |
| 2 | 1 | High |
| 5 | 1 | Very high |
| 10 | 1 | Extremely high |

[FIG. 5]

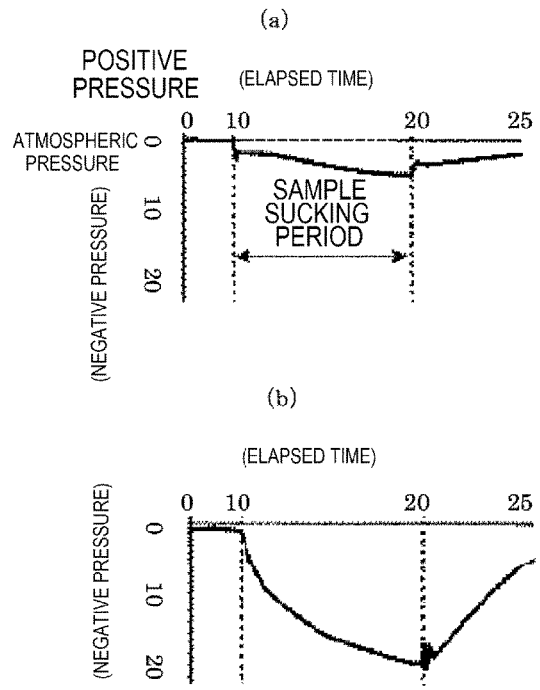

[FIG. 6]

| First dispensed liquid | | Amount of secondarily dispensed liquid | Discharge speed |
|---|---|---|---|
| Dispensing amount | Viscosity | | |
| 1 | High | 10 | Very low |
| | Low to medium | | Extremely low |
| 1 | High | 5 | Low |
| | Low to medium | | Very low |
| 1 | High | 2 | Medium |
| | Low to medium | | Low |
| 1 | Low to medium | 1 | Medium |
| 2 | High | 1 | Very high |
| | Low to medium | | High |
| 5 | High | 1 | Extremely high |
| | Low to medium | | Very high |
| 10 | High | 1 | Extremely high |
| | Low to medium | | Extremely high |

[FIG. 7]
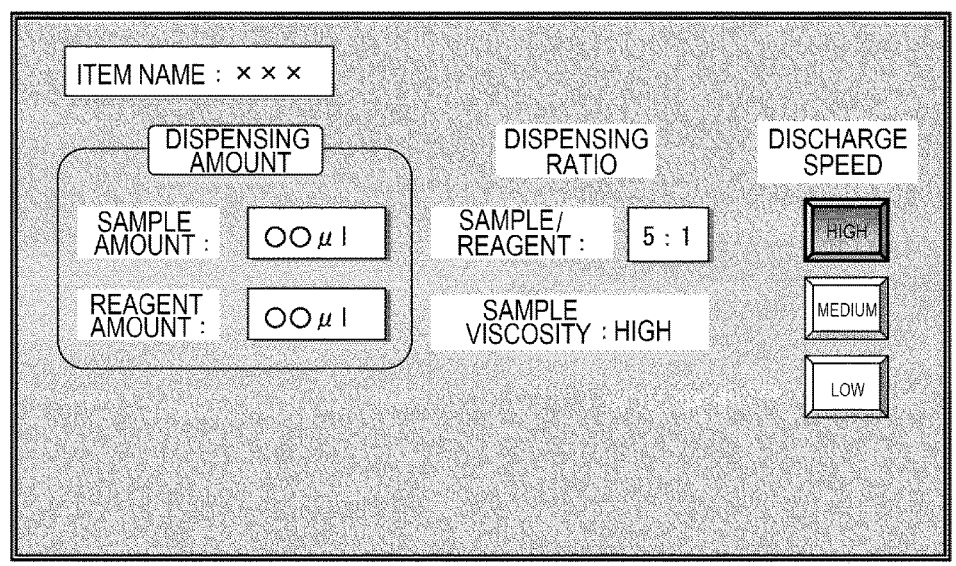

AUTOMATED ANALYZER

TECHNICAL FIELD

The present invention relates to an automated analyzer which automatically analyzes a component of a biological sample such as blood, and particularly relates to a method of stirring a sample and a reagent used for the measurement of blood coagulation such as a blood agglutination reaction, or the like.

BACKGROUND ART

As an analyzer which analyzes the amount of a component contained in a sample, there has been known an automated analyzer which measures a change in transmitted light intensity or scattered light intensity at a single wavelength or multiple wavelengths obtained by irradiating light from a light source onto a reaction solution obtained by mixing a sample with a reagent, and calculates the amount of a component based on the relationship between the light intensity and the concentration.

In the reaction of the reaction solution, there are roughly two types of analysis fields as follows: a colorimetric analysis using a color reaction between a substrate and an enzyme; and a homogeneous immunoassay using an agglutination reaction by binding between an antigen and an antibody. As the latter homogeneous immunoassay, measurement methods such as an immunonephelometric method and a latex agglutination method are known. Further, there is also known a heterogeneous immunoassay device which performs an immunoassay with higher sensitivity by employing a detection technique using chemiluminescence or electrochemical luminescence and a B/F separation technique.

In addition, there also exists an automated analyzer which measures blood coagulability. Blood maintains its fluidity in blood vessels and flows therethrough. However, once bleeding occurs, a coagulation factor present in plasma or platelets is activated in a chain reaction, and fibrinogen in plasma is converted into fibrin, and the fibrin is deposited, whereby bleeding is arrested.

Such blood coagulability includes an extrinsic one in which blood leaking outside the blood vessel coagulates and an intrinsic one in which blood coagulates in the blood vessel. The measurement items with respect to blood coagulability (blood coagulation time) include a prothrombin time (PT) in an extrinsic blood coagulation reaction test, an activated partial thromboplastin time (APTT) and a fibrinogen level (Fbg) in an intrinsic blood coagulation reaction test, and the like.

All these items are measured by detecting fibrin deposited by adding a reagent to start coagulation using an optical, physical, or electrical technique. As the method using an optical technique, there is known a method in which light is irradiated onto a reaction solution, and fibrin deposited in the reaction solution is detected as a change in the intensity of scattered light or transmitted light over time, whereby the time when fibrin starts to deposit is calculated. The coagulation time in a blood coagulation reaction (particularly, the item of Fbg) is as short as several seconds, and therefore, it is necessary to perform photometry at short intervals of about 0.1 seconds, and also when the reaction solution is coagulated, the reaction container cannot be recycled by cleaning, and therefore, the reaction is performed in an independent photometric port, and the reaction container is disposable. Further, the reaction time starts immediately, and therefore, many devices are configured such that stirring using a stirrer which is performed in the above-described colorimetric analysis, homogeneous immunoassay, or the like is not performed, but stirring is performed by a pressure generated when a sample or a reagent is discharged to effect the reaction, and a change in light intensity is measured. Further, it is essential for the automated analyzer to perform measurement with high reproducibility and high reliability. Accordingly, even in the case where the reaction solution is stirred by a discharge pressure, it is necessary to mix the entire reaction solution uniformly with good reproducibility and effect the reaction.

According to PTL 1, a reaction container is disposed in a holding member which performs conical rotational motion, and immediately after it is detected that a reagent is dispensed therein, the reaction container is rotated for each holding member, whereby the sample and the reagent are stirred. According to this method, a mechanism of rotating the reaction container is needed, and therefore, it is assumed that the number of components is increased, the structure is complicated, and the cost of the device is increased.

Also in PTL 2, a sample and a reagent are stirred by shaking a reaction container similarly. In this case, a pendulum motion, a reciprocating motion, an eccentric rotational motion, or a compound motion by combining two or more of these motions is performed. It is considered that in this case, stirring can be performed more uniformly with higher reproducibility than in (PTL 1) by a complicated motion, however, it cannot be denied that the structure is complicated for that.

In PTL 3, when a reagent is dispensed in a sample in a specimen container, suction and discharge of the sample are alternately repeated several times by a reagent dispensing probe at the time point when the reagent dispensing probe reached the liquid surface of the sample by employing the detection of the liquid surface, whereby the sample is stirred. It is considered that in this case, stirring can be presumably performed efficiently, however, the possibility of contamination of the reagent probe with the sample is high. Further, in the case of a device in which a specimen container or a reaction container is held in a rotary disk, it is necessary to perform the suction and discharge operations by stopping the rotation of the disk for a given time, and therefore, the processing ability may be decreased.

CITATION LIST

Patent Literature

PTL 1: JP-A-10-73540
PTL 2: JP-A-10-73532
PTL 3: JP-A-2011-128075

SUMMARY OF INVENTION

Technical Problem

In the case of a device in which a sample and a reagent are mixed with each other to cause blood coagulation or the like, and a time when a coagulation reaction is optically detected is measured, generally, a time until an optical change starts is short, and there is no time to perform stirring using a stirrer, or there is a fear that the reaction is inhibited by the insertion of the stirrer into the reaction solution, and therefore, a non-contact stirring method is adopted in many cases. As the non-contact stirring method, there are various methods, for example, a reaction container is shaken, stirring is performed by ultrasound, etc., however, as a method which is inexpensive and in which the structure is relatively simple, a method of performing stirring by the discharge pressure of a liquid is generally used, and many devices adopt this method.

In the case of performing stirring by a discharge pressure, it is considered that if the discharge pressure is simply maintained high, sufficient stirring can be performed, however, when a change in light intensity is measured, if foaming occurs in the reaction solution, the measurement is inhibited, and therefore, the occurrence of foaming should be absolutely avoided. However, in the case where the pressure is excessively decreased in order to avoid foaming so that stirring is performed non-uniformly due to an insufficient discharge pressure, it is difficult to measure the reaction accurately.

On the other hand, the amount of a sample and the amount of a reagent vary depending on the item, and mixing of the sample and the reagent may be difficult in some cases depending on the combination thereof. For example, in the case where the amount of a sample which is previously dispensed into a reaction container is larger than that of a reagent to be dispensed subsequently, it is presumed that sufficient stirring cannot be performed by the discharge pressure of the reagent, and in the opposite case, there is a concern that foaming may occur. Therefore, it is necessary to perform stirring by a pressure and a discharge method such that foaming should be absolutely avoided while uniformly causing the reaction of the entire reaction solution.

Further, since the viscosity of a sample varies depending on individuals, in the case of performing stirring with a sample with a high viscosity even under the above-described conditions, stirring is still insufficient at the same speed, and therefore, it is presumed that the reaction occurs non-uniformly. Accordingly, in order to provide measurement data with high reliability, it is necessary to perform stirring by a pressure and a discharge method capable of obtaining data with high reproducibility under the conditions of respective combinations for the ratio of the amount of the sample to the amount of the reagent, and also the relationship thereof with the viscosity of the sample.

Solution to Problem

A representative configuration of the invention is as follows.

An automated analyzer is configured to include: a reaction container which allows a sample and a reagent to react with each other; a detection section which detects light irradiated onto a reaction solution in the reaction container; a reagent dispensing mechanism which dispenses the reagent into the reaction container; a sample dispensing mechanism which dispenses the sample into the reaction container; and a control section which controls the reagent dispensing mechanism and the sample dispensing mechanism, wherein the control section causes one dispensing mechanism of either the reagent dispensing mechanism or the sample dispensing mechanism to first discharge a predetermined amount of a liquid into the reaction container, and then, with respect to the cases where the amount of a liquid to be discharged by the other dispensing mechanism is larger or smaller than the amount of the liquid in the reaction container, causes the other dispensing mechanism to discharge the liquid such that the discharge speed in the case where the amount of the liquid to be discharged is larger is decreased relative to the discharge speed in the case where the amount of the liquid to be discharged is smaller.

Further, the automated analyzer is configured such that a pressure sensor which can observe a variation in pressure in a flow channel is provided for the sample dispensing mechanism, and the sample or the reagent is discharged by changing the discharge speed of the sample or the reagent depending on the viscosity obtained from the variation in pressure when sucking the sample.

The configuration is not limited to one described below, however, as an example of the automated analyzer, the automated analyzer includes: multiple detection sections, each provided with a reaction container placement section in which the reaction container which allows a sample and a reagent to react with each other is placed; a light source which irradiates light provided on the bottom or side of the reaction container placement section; and a detector which is provided for the reaction container placement section and detects scattered light from the reaction container of the light irradiated from the light source. In the case where the light source is provided on the bottom, the detector is disposed on the side of the reaction container and receives scattered light from the bottom. In the case where the light source is provided on the side of the reaction container, the detector is disposed at a position where the detector receives light orthogonal to the light from the light source.

Further, a container and a mechanism for retaining a sample are provided, and similarly a container and a mechanism for retaining a reagent are provided, and reagent and sample probes and syringe pumps which serve as the dispensing mechanisms movable in the vertical and rotational directions or the horizontal direction, and are capable of accurately dispensing the reagent and the sample are provided, and the sample and the reagent are respectively dispensed into the reaction container from the dispensing mechanisms. By first dispensing one of either the sample or the reagent into the reaction container, and subsequently dispensing the other one into the container, the reaction solution is stirred. A blood coagulation reaction time is measured based on a change in light intensity in this reaction solution. Further, an operation section connected to the device is provided, and on an operation screen, a dispensing amount, a dispensing speed, a dispensing ratio, etc. are displayed, and it is also possible to change the dispensing speed on the operation screen.

Further, from a variation in pressure when sucking the sample, the viscosity level of the sample or the like is displayed on the screen, and a dispensing speed previously set according to the viscosity is displayed. If any need arises, the dispensing speed may be able to be changed on the operation screen.

Incidentally, by stirring the sample and the reagent by a discharge pressure in the dispensing mechanism without using other stirring methods, a measurement result with high accuracy can be obtained with a relatively simple structure.

Advantageous Effects of Invention

According to the invention, it is possible to reduce foaming of the reaction solution, and also to uniformly stir the entire reaction solution. Due to this, the non-uniformity of blood agglutination reaction measurement can be suppressed, and a measurement result with high accuracy can be obtained.

BRIEF DESCRIPTION OF DRAWINGS

FIG. 1 is a schematic view of a general automated blood coagulation analyzer.

FIG. 2 shows a dispensing and stirring method for a general blood coagulation item.

FIG. 3 shows an example of the control of a discharge speed of the invention.

FIG. 4 shows the example of the control of a discharge speed of the invention.

FIG. 5 shows an example of a variation in pressure when sucking the sample.

FIG. 6 shows an example of the control of a discharge speed of the invention.

FIG. 7 shows an example of the display on a screen of the invention.

DESCRIPTION OF EMBODIMENTS

FIG. 1 shows one example of the configuration of a general blood coagulation analyzer. The functions of the respective sections are known, and therefore, a detailed description thereof will be omitted. The device is configured as follows. A sampling arm 102 of a sampling mechanism 101 moves up and down and also rotates, and by using a sample dispensing probe 103 attached to the sampling arm 102, a sample in a sample container 105 disposed in a sample disk 104 which rotates right and left is sucked and discharged into a reaction container 106. The sample dispensing probe 103 performs an operation of sucking a sample and an operation of discharging a sample accompanying the operation of a sample syringe pump 107. Incidentally, in a flow channel, a pressure sensor 130 is provided and monitors mainly a variation in pressure when sucking the sample. A reagent dispensing mechanism 108 is similarly configured such that a reagent dispensing arm 109 moves up and down and also rotates, and a reagent dispensing probe 110 sucks a reagent in a reagent container 112 disposed in a reagent disk 111 and discharges the reagent into the reaction container 106, and a reagent heating mechanism 113 is included therein. The sample and the reagent discharged into the reaction container 106 are reacted with each other. The reagent dispensing probe 110 performs an operation of sucking a reagent and an operation of discharging a reagent accompanying the operation of a reagent syringe pump 114. The reaction container 106 is held by a reaction container holding section 118 of a rotatable reaction container carrying mechanism 117 from a reaction container stock section 115, and rotationally moves, and then is placed in a reaction container placement section 120 of a detection section 119. The reaction container placement section 120 is provided with a cavity so that the reaction container 106 can be placed therein, and in this cavity, the reaction container 106 can be inserted. Further, although not shown in the drawing, this reaction container placement section 120 is provided more than one, and this device includes multiple detection sections 119. The reaction container carrying mechanism 117 is a mechanism which is configured to hold the reaction container 106 and carry and place the reaction container 106, and is common to the multiple detection sections.

Next, the flow of the measurement will be described. First, an analysis item to be analyzed for each sample is input from an input device such as a key board 121 or a screen of a CRT 122. The operation of a unit is controlled by a computer (a control section) 123. By the sample dispensing mechanism 101, a sample in the sample container 105 disposed in the sample disk 104 is sucked and dispensed into the reaction container 106 placed in the reaction container placement section 120 in the detection section 119. Subsequently, a reagent is also similarly sucked from the reagent container 112 disposed in the reagent disk 111 by the reagent dispensing mechanism 108, and the reagent is heated to an appropriate temperature by the reagent heating mechanism 113, and dispensed into the reaction container 106. By the discharge pressure of this reagent, a blood coagulation reaction is started promptly. Light from a light source 124 is irradiated onto the reaction container 106, and scattered light scattered by the reaction solution in the reaction container is detected by the detection section 125 such as a photodiode, and a photometric signal is input to the computer (control section) 123 through an interface 127 via an A/D converter 126, and a coagulation reaction time is calculated. The result is output as a print by a printer 128 through the interface 127 or output on a screen of the CRT 122, and also stored in a hard disk 129 as a memory. The reaction container 106 after photometry is completed is held by the reaction container carrying mechanism 117 and discarded to the reaction container discarding section 116.

FIG. 2 shows one example of a dispensing method in the blood coagulation reaction measurement. As shown in FIG. 2, in a device which causes a reaction by stirring a reaction solution for blood coagulation or the like by only a discharge pressure of a liquid, one of either a sample 202 or a reagent 203 is previously dispensed into a reaction container 200 using a dispensing probe 201, and subsequently, the rest of the other one is dispensed into the container. At this time, by the discharge pressure of the liquid dispensed secondarily, the sample and the reagent are mixed and stirred in the reaction container, and a reaction proceeds. However, there is not only a case where one type of reagent is dispensed, but also a case where multiple types of reagents are dispensed. Further, the mixing ratio of the sample to the reagent vary such that the amounts of the sample and the reagent are substantially the same, the amount of the sample is larger than that of the reagent, and the amount of the reagent is larger than that of the sample.

Next, a method of stirring a sample and a reagent will be described. The amount required for an item is from about 5 to 50 µl, in the case of a sample and from about 20 to 250 µl, in the case of a reagent, and the combination of the amounts vary depending on the item or the like. In the case where the amounts of the sample and the reagent are substantially the same, uniform mixing is considered to be relatively easy, however, in the case where the amount of a liquid dispensed first is larger than the amount of a liquid to be discharged subsequently, mixing is more difficult as compared with the case where the amounts are substantially the same. On the other hand, in the case where the amount of a liquid dispensed first is smaller than the amount of a liquid to be discharged subsequently, although it depends on the property of the liquid, foaming is likely to occur depending on the discharge speed. Therefore, by making the discharge speed variable depending on the liquid amounts of the sample and the reagent, a reaction which is uniform and free from disturbance such as foam is accelerated, and as a result, it becomes possible to perform measurement with higher reliability.

FIG. 3 is a graph showing one example of the control of a discharge speed. The ordinate represents a coagulation time, and the abscissa represents a discharge speed. Incidentally, the discharge amount is constant. An average of the data of n-times measurements is calculated, and the maximum and minimum values are shown as an error bar. In an area where the discharge speed is low (the discharge speed is less than 6) on the left side of the graph, the coagulation time and the discharge speed are in inverse proportion to each other, and the data is not stable, and therefore, it is found that sufficient stirring is not performed. In an area of intermediate values (the discharge speed is from 6 to 7) in the graph, the coagulation time is stable, and also a variation in data is small, and therefore, it is considered that sufficient stirring was performed, and stable data was obtained. However, when the discharge speed is further increased (the discharge speed is 7.5 or more), although the coagulation time is equivalent to that described above, the variation width of the data is increased. It is considered that this is because due to the discharge pressure, foam was mixed in the reaction solution and affected the optical change, and thus, the variation was increased. Accordingly, when the discharge speed is relatively changed based on the mixing ratio of the sample to the reagent, it is necessary to relatively perform control by selecting the discharge speed which provides the best data reproducibility according to the respective discharge conditions.

FIG. 4 is a table showing one example of the control of the discharge speed using the mixing ratio of the sample to the reagent, and shows simplified control with reference to the above results. In the table, in the case where the discharge speed is set to medium at a mixing ratio of 1:1, the discharge speed is set extremely low, very low, low, medium, high, very high, and extremely high in order from the top. As already described in the description of FIG. 3, the respective speeds are determined within the range of the speed which provides the best data reproducibility according to the respective conditions.

In FIG. 4, a case of seven discharge speed levels is shown, however, the discharge speed levels are not limited to the seven discharge speed levels, and the advantageous effect of the invention can be obtained even in the case of a change between two discharge speed levels such that the control section causes one dispensing mechanism of either the reagent dispensing mechanism or the sample dispensing mechanism to first discharge a predetermined amount of a liquid (the amount of a first dispensed liquid) into the reaction container, and then, with respect to the cases where the amount of a liquid to be discharged by the other dispensing mechanism (the amount of a secondarily dispensed liquid) is larger or smaller than the amount of the liquid in the reaction container, causes the other dispensing mechanism to discharge the liquid such that the discharge speed in the case where the amount of the liquid to be discharged is larger is decreased relative to the discharge speed in the case where the amount of the liquid to be discharged is smaller. Further, a change among three discharge speed levels is desirable. That is, the control section desirably performs the control at three or more discharge speed levels depending on the mixing ratio of the sample to the reagent.

FIG. 5 shows one example of a variation waveform, when sucking the sample, of the pressure sensor 130 provided for a sample sucking mechanism. FIG. 5(a) shows an example of a waveform when sucking a normal or general specimen. Simultaneously with the start of sucking of the sample, the pressure is decreased, and in a sample sucking period, the pressure is gently changed. Then, after the sucking is completed, the pressure on the negative pressure side returns to the atmospheric pressure. FIG. 5(b) shows an example of a waveform when sucking a sample with a high viscosity. As compared with the waveform shown in FIG. 5(a), the pressure is largely changed to the negative pressure side in the sucking period, and also, even when the sucking period is completed, a time until the pressure returns to the atmospheric pressure is long.

The change in pressure at this time is affected by the properties of the sample such as the viscosity or density of the sample, or the sucking speed. Therefore, if the sucking speed is constant, the degree of the viscosity or density of the sample appears as the waveform, and thus, a variation in pressure is effective as a factor showing the viscosity level.

FIG. 6 shows an example of the method of controlling the dispensing speed by adding a parameter of the viscosity of the sample in the case where the first dispensed liquid is determined to be the sample in FIG. 4. The viscosity of the sample varies depending on individuals, and mixing of a sample with a high viscosity is more difficult than a sample with a standard viscosity, and therefore, the possibility of resulting in insufficient stirring is high. Therefore, it is necessary to perform the control of not only the discharge speed depending on the ratio of the amounts of the sample and the reagent, but also the discharge speed in further consideration of the viscosity of the sample.

If the viscosity of the sample is high based on the result of a variation in pressure when sucking the sample, as shown in FIG. 6, in the case where the dispensing amount of the first dispensed liquid which is determined to be the sample is set to 1, and the amount of the secondarily dispensed liquid (reagent to be dispensed) is set to 5, the discharge speed is set low, although the discharge speed is set very low in FIG. 4 in which the viscosity is not considered.

Similarly, in the case where the amount of the first dispensed liquid (sample) is set to 5, and the amount of the secondarily dispensed liquid (reagent) is set to 1, if the viscosity of the sample is high, the discharge speed is set extremely high, although the discharge speed is set very high in FIG. 4. By doing this, it becomes possible to perform optimum stirring while suppressing insufficient stirring.

In the case where the amount of the secondarily dispensed liquid is larger with respect to the ratio of the liquid amounts, even if the ratio of the liquid amounts is the same, when the viscosity of the first dispensed liquid is relatively high, the discharge speed is changed from extremely low to very low, from very low to low, or from low to medium. That is, the control section causes the reagent to be discharged by setting the discharge speed relatively higher. On the other hand, in the case where the amount of the secondarily dispensed liquid is smaller with respect to the ratio of the liquid amounts, even if the ratio of the liquid amounts is the same, when the viscosity of the first dispensed liquid is relatively high, the discharge speed is changed from high to very high, or from very high to extremely high. That is, the control section causes the reagent to be discharged by setting the discharge speed relatively higher.

In this manner, the stirring performance is further improved by changing the speed of the discharge depending not only on the dispensing ratio of the sample to the reagent, but also on the viscosity of the sample.

That is, the stirring performance can be further improved by changing the discharge speed using the mixing ratio of the sample to the reagent and the viscosity of the sample as parameters.

FIG. 7 shows an example of the display on a screen of a discharge speed, a dispensing ratio, etc. Here, a display example in the case where the sample is first discharged into the reaction container and the reagent is subsequently dispensed is shown. For example, when or immediately after an analysis request is input, the name of an item, and the dispensing amounts of the sample and the reagent are displayed on a screen as shown in FIG. 7. Then, the dispensing ratio is automatically calculated and displayed. Further, according to the relationship between the dispensing ratio and the liquid properties of the reagent, etc., the discharge speed or the level of the discharge speed is automatically selected based on the predetermined setting and displayed on the screen. In FIG. 7, the level of the discharge speed is displayed by the following three levels: high; medium; and low, however, the discharge speed may be displayed by a numerical value.

Further, in the case where it is necessary to discharge a liquid at a speed other than the automatically set discharge speed for some reasons, for example, research or the like, the discharge speed may be able to be changed by selecting the discharge speed from the selection buttons on the screen. Incidentally, the speed may be changed by the selection buttons or by inputting a numerical value on the screen. However, in the case where such a change of the discharge speed is not necessary or strictly prohibited, a configuration in which the speed is only displayed, and a change of the speed cannot be performed may be adopted.

Further, the viscosity of the sample calculated from a variation in pressure when sucking the sample is displayed on the screen, and based on the predetermined setting, the discharge speed or the level of the discharge speed is automatically selected and displayed on the screen. Also in this case, similarly, the viscosity may be displayed by the level such as high or medium, or the calculated viscosity value may be displayed.

REFERENCE SIGNS LIST

101: sampling mechanism, 102: sampling arm, 103: sample dispensing probe, 104: sample disk, 105: sample container, 106: reaction container, 107: sample syringe pump, 108: reagent dispensing mechanism, 109: reagent dispensing arm, 110: reagent dispensing probe, 111: reagent disk, 112: reagent container, 113: reagent heating mechanism, 114: reagent syringe pump, 115: reaction container supply section, 116: reaction container discarding section, 117: reaction container carrying mechanism, 118: reaction container holding section, 119: detection section, 120: reaction container placing position, 121: keyboard, 122: CRT, 123: computer, 124: light source, 125: detector, 126: A/D converter, 127: interface, 128: printer, 129: memory, 130: pressure sensor, 200: reaction container, 201: dispensing probe, 202: sample, 203: reagent

The invention claimed is:

1. An automated analyzer, comprising:
   a reaction container;
   a sample dispensing mechanism which dispenses the sample into the reaction container;
   a reagent dispensing mechanism which dispenses the reagent into the reaction container;
   a detection section which detects light irradiated onto a reaction solution of the sample and the reagent in the reaction container; and
   a control section which controls the reagent dispensing mechanism and the sample dispensing mechanism,
   wherein the control section is programmed to cause the sample dispensing mechanism to first discharge a predetermined amount of the sample into the reaction container, and then, when an amount of the reagent to be discharged by the reagent dispensing mechanism is larger than the amount of the sample in the reaction container, cause the reagent dispensing mechanism to discharge the reagent at a first discharge speed, and, when the amount of the reagent to be discharged by the reagent dispensing mechanism is smaller than the amount of the sample in the reaction container, cause the reagent dispensing mechanism to discharge the reagent at a second discharge speed greater than the first discharge speed.

2. The automated analyzer according to claim 1,
   wherein the control section is programmed to select the first discharge speed and the second discharge speed of the reagent dispensing mechanism from among three or more discharge speed levels based on a mixing ratio of the amount of the sample to the amount of the reagent.

3. The automated analyzer according to claim 2, further comprising:
   a display connected to the control unit,
   wherein the control unit is programmed to cause the mixing ratio of the sample to the reagent to be displayed on an operation screen of the display.

4. The automated analyzer according to claim 3,
   wherein the control unit is programmed to cause the selected first discharge speed or the selected second discharge speed to be displayed on the operation screen.

5. The automated analyzer according to claim 4,
   wherein one of the selected first discharge speed or the selected second discharge speed is changed from on the operation screen.

6. The automated analyzer according to claim 1,
   wherein the sample and the reagent are stirred by a discharge pressure of the reagent dispensed by the reagent dispensing mechanism without using other stirring methods.

7. The automated analyzer according to claim 1, further comprising:
   a pressure sensor which monitors a variation in pressure when sucking the sample with the sample dispensing mechanism,
   wherein the control unit is programmed to change the first discharge speed and the second discharge speed of the reagent based on a viscosity level of the sample obtained from the variation in pressure monitored by the pressure sensor.

8. The automated analyzer according to claim 7,
   wherein the control unit is programmed to select the first discharge speed and the second discharge speed of the reagent dispensing mechanism from among three or more discharge speed levels based on a mixing ratio of the sample to the reagent and the viscosity level of the sample.

9. The automated analyzer according to claim 7, further comprising:
   a display connected to the control unit,
   wherein the control unit is programmed to cause a mixing ratio of the sample to the reagent and the viscosity level of the sample to be displayed on an operation screen of the display.

10. An automated analyzer, comprising:
    a reaction container;
    a sample dispensing mechanism which dispenses the sample into the reaction container;
    a reagent dispensing mechanism which dispenses the reagent into the reaction container;
    a detection section which detects light irradiated onto a reaction solution of the sample and the reagent in the reaction container; and
    a control section which controls the reagent dispensing mechanism and the sample dispensing mechanism,
    wherein the control section is programmed to cause the reagent dispensing mechanism to first discharge a predetermined amount of the reagent into the reaction container, and then, when an amount of the sample to be discharged by the sample dispensing mechanism is larger than the amount of the reagent in the reaction container, cause the sample dispensing mechanism to discharge the sample at a first discharge speed, and, when the amount of the sample to be discharged by the sample dispensing mechanism is smaller than the amount of the sample in the reaction container, cause the sample dispensing mechanism to discharge the sample at a second discharge speed greater than the first discharge speed.

11. The automated analyzer according to claim 10, wherein the control section is programmed to select the first discharge speed and the second discharge speed of the sample dispensing mechanism from among three or more discharge speed levels based on a mixing ratio of the amount of the sample to the amount of the reagent.

12. The automated analyzer according to claim 11, further comprising:
a display connected to the control unit,
wherein the control unit is programmed to cause the mixing ratio of the sample to the reagent to be displayed on an operation screen of the display.

13. The automated analyzer according to claim 12, wherein the control unit is programmed to cause the selected first discharge speed or the selected second discharge speed to be displayed on the operation screen.

14. The automated analyzer according to claim 13, wherein one of the selected first discharge speed or the selected second discharge speed is changed from on the operation screen.

15. The automated analyzer according to claim 10, wherein
wherein the sample and the reagent are stirred by a discharge pressure of the sample dispensed by the sample dispensing mechanism without using other stirring methods.

16. The automated analyzer according to claim 10, further comprising:
a pressure sensor which monitors a variation in pressure when sucking the reagent with the reagent dispensing mechanism,
wherein the control unit is programmed to change the first discharge speed and the second discharge speed of the sample based on a viscosity level of the reagent obtained from the variation in pressure monitored by the pressure sensor.

17. The automated analyzer according to claim 16, wherein the control unit is programmed to select the first discharge speed and the second discharge speed of the reagent dispensing mechanism from among three or more discharge speed levels based on a mixing ratio of the sample to the reagent and the viscosity level of the reagent.

18. The automated analyzer according to claim 16, further comprising:
a display connected to the control unit,
wherein the control unit is programmed to display a mixing ratio of the sample to the reagent and the viscosity level of the reagent on an operation screen of the display.

19. An automated analyzer, comprising:
a reaction container;
a first dispensing mechanism which dispenses one of a sample or a reagent as a first liquid into the reaction container;
a second dispensing mechanism which dispenses which dispenses the other one of the sample or the reagent as a second liquid into the reaction container;
a detection section which detects light irradiated onto a reaction solution of the first liquid and the second liquid in the reaction container; and
a control section which controls the first dispensing mechanism and the second dispensing mechanism,
wherein the control section is programmed to cause the first dispensing mechanism to first discharge a predetermined amount of the first liquid into the reaction container, and then, when an amount of the second liquid to be discharged by the reagent dispensing mechanism is larger than the amount of the first liquid in the reaction container, cause the second dispensing mechanism to discharge the second liquid at a first discharge speed, and, when the amount of the second liquid to be discharged by the second dispensing mechanism is smaller than the amount of the first liquid in the reaction container, cause the second dispensing mechanism to discharge the second liquid at a second discharge speed higher than the first discharge speed.

* * * * *